(12) United States Patent
Kim et al.

(10) Patent No.: US 10,507,312 B2
(45) Date of Patent: Dec. 17, 2019

(54) METHOD FOR MANUFACTURING MICRONEEDLE

(71) Applicant: Raphas Co., Ltd., Seoul (KR)

(72) Inventors: Jung Dong Kim, Seoul (KR); Do Hyeon Jeong, Seoul (KR); Beom Joon Kim, Tokyo (JP); Hong Kee Kim, Gyeonggi-do (KR)

(73) Assignee: Raphas Co., Ltd., Seoul (KR)

( * ) Notice: Subject to any disclaimer, the term of this patent is extended or adjusted under 35 U.S.C. 154(b) by 0 days.

(21) Appl. No.: 15/927,389

(22) Filed: Mar. 21, 2018

(65) Prior Publication Data

US 2018/0207415 A1 Jul. 26, 2018

Related U.S. Application Data

(63) Continuation of application No. PCT/KR2017/004058, filed on Apr. 14, 2017.

(30) Foreign Application Priority Data

May 20, 2016 (KR) .................. 10-2016-0061903

(51) Int. Cl.
*A61M 37/00* (2006.01)
*H01J 37/32* (2006.01)

(52) U.S. Cl.
CPC ......... *A61M 37/0015* (2013.01); *H01J 37/32* (2013.01); *A61M 2037/0053* (2013.01)

(58) Field of Classification Search
CPC ....... A61M 37/0015; A61M 2037/0053; H01J 37/32
See application file for complete search history.

(56) References Cited

U.S. PATENT DOCUMENTS

| 3,507,650 A | * | 4/1970 | Land | ............... G03B 17/50 |
| | | | | 118/246 |
| 2011/0240201 A1 | * | 10/2011 | Jung | ............. A61M 37/0015 |
| | | | | 156/60 |
| 2019/0046778 A1 | * | 2/2019 | Jin | ....................... A61K 9/00 |

FOREIGN PATENT DOCUMENTS

KR    100938631 B1 * 1/2010
KR    101285085 B1 * 7/2013

OTHER PUBLICATIONS

KR-100938631-B1 Machine Translation of Description (EPO/Google).*
KR101285085(B1) published Jul. 17, 2013 Machine Translation of Description (EPO/Google).*

* cited by examiner

*Primary Examiner* — Christopher T Schatz
*Assistant Examiner* — Cynthia L Schaller
(74) *Attorney, Agent, or Firm* — Mintz Levin Cohn Ferris Glovsky and Popeo, P.C.; Jhongwoo Peck

(57) ABSTRACT

The present disclosure relates to a method for manufacturing a microneedle enabling product quality and efficiency in production to be improved by reducing the time needed for spotting a viscous material. The method for manufacturing a microneedle, according to the present disclosure, comprises the steps of spotting a viscous material on a plurality of spots on a film by supplying the viscous material to the upper surface of the film by means of a plurality of through-holes provided on an injection plate, elongating the viscous material spotted on the film; and coagulating the elongated viscous material.

1 Claim, 11 Drawing Sheets

METHOD FOR MANUFACTURING MICRONEEDLE

CROSS-REFERENCE TO RELATED APPLICATIONS

This application is a continuation application of International Application No. PCT/KR2017/004058 filed on Apr. 14, 2017, which claims priority to Korean Application No. 10-2016-0061903 filed on May 20, 2016. The applications are incorporated herein by reference.

TECHNICAL FIELD

The present disclosure relates to a method of manufacturing a microneedle, and more particularly, to a method of manufacturing a microneedle which is inserted into skin for supplying drugs or nutrients in the body.

RELATED ART

Although a great number of drugs and bioactive substances for treating diseases has been developed, it is challenging to deliver the drugs and bioactive substances into the body due to a biological barrier, for example, skin, oral mucosa, and brain-blood barrier and thus, problems regarding passing through the biological barrier and delivery of drugs still remain.

In general, drugs and bioactive substances are orally administered in the form of tablets or capsules. However, various drugs are digested or absorbed in the gastro-intestinal tract or lost due to a liver mechanism and accordingly, the drugs and bioactive substances may not be efficiently delivered. In addition, several drugs pass through intestinal mucous membrane and may not be effectively spread. Patient's compliance is also an issue (for example, if a patient needs to take medicine in a regular interval, or critical patents who cannot take medicine).

Other general way of delivering drugs and bioactive substances is a use of needles. It is a more efficient way than oral administration, however, may cause pain on injection sites, a local damage on skin, bleeding, and disease infection on injection sites.

In order to solve problems of oral administration and subcutaneous injection, transdermal administration using patches are used. In the transdermal administration using patches, patient compliance is high, and drug level in blood remains steady. However, skin-permeable drugs are limited, and drug delivery rate is low.

Accordingly, various micro structures including microneedles are developed. The microneedles developed until the present are mainly used in delivering drugs in the body, blood-gathering, and detecting analyte in the body.

On the other hand, a completely new method of manufacturing a micro structure is disclosed in Korean Patent Application No. 10-2010-0130169 (title of the disclosure: Method of manufacturing a micro structure, hereinafter, referred to as a prior art) by the same applicant. In the prior art, a viscous material is spotted in drops on a substrate by using a nozzle and then, the viscous material contacts with another substrate or a viscous material spotted on the other substrate. Then, the contacted viscous material is elongated and coagulated. In addition, according to such a method, sufficient hardness is realized and a loss of functional materials is reduced.

However, since the viscous material is spotted in drops on a substrate in the prior art, the time required for spotting a number of viscous materials on a substrate increases and thereby, the entire process time increases. Therefore, productivity is reduced.

Also, when the spotting time becomes longer, a part of the viscous material that is already spotted evaporates. Thus, a difference in viscosity between the viscous materials may occur and thereby, a deviation in a length of microneedles or a thickness of the top of the microneedles becomes worse. Therefore, the defect rate of products is increased. In particular, when a thickness of the top of the microneedle increases, efficiency of skin penetration lowers and thereby, drug delivery rate lowers. Further, as the thickness of the top of the microneedle increases, patients experience more severe pain and thus, the users of the products feel uncomfortable.

In addition, according to the method of manufacturing a micro structure in the prior art, a force to combine the surface of the substrate and the viscous material together is needed for elongating and separating and thus, usable viscous materials are limited based on the characteristics of the surface of the substrate.

The above information disclosed in this section is merely for enhancement of understanding of the background of the invention and therefore it may contain information that does not form the prior art that is already known in this country to a person of ordinary skill in the art.

SUMMARY

The present disclosure provides a method of manufacturing a microneedle by which the time required to spot a viscous material may be reduced and thereby, quality of products and production efficiency may be increased.

In order to solve the technical problem, the present disclosure provides a method of manufacturing a microneedle made by spotting a viscous material on a plurality of points on a film by supplying the viscous material on a upper surface of the film through a plurality of through holes disposed on an injection plate, elongating the viscous material spotted on the film, and coagulating the elongated viscous material. The method may further include a step of surface modifying the film to increase an adhesive force between the viscous material and the film before spotting of the viscous material, wherein the surface modifying may be performed by a plasma treatment. In the spotting, the viscous material may be supplied while the injection plate is closely adhered to the upper surface of the film. In addition, the injection plate may be surface treated to lower the adhesive force between the injection plate and the viscous material, and the through holes of the injection plate may have widths which become gradually narrower as they go from the upper surface toward the lower surface.

In another exemplary embodiment, the method of manufacturing a microneedle may include the steps of disposing a mask with a plurality of through holes on a film, surface modifying the surface of the film that corresponds to the through holes by plasma treating the film to increase an adhesive force between the film and the viscous material, contacting the surface modified film with the viscous material and separating the film so as for the viscous material to be adhered to the surface modified part of the film, elongating the viscous material adhered to the film, and coagulating the elongated viscous material.

The present disclosure provides a method for manufacturing a microneedle enabling product quality and efficiency in production to be improved by reducing the time needed for spotting a viscous material.

BRIEF DESCRIPTION OF THE DRAWINGS

The above and other features and advantages of the present disclosure will become more apparent by describing in detail exemplary embodiments thereof with reference to the attached drawings in which.

DETAILED DESCRIPTION OF TH EMBODIMENTS

The present disclosure will be described more fully hereinafter with reference to the accompanying drawings, in which exemplary embodiments of the disclosure are shown. While the disclosure will be described in conjunction with exemplary embodiments, it will be understood that present description is not intended to limit the disclosure to those exemplary embodiments. On the contrary, the disclosure is intended to cover not only the exemplary embodiments, but also various alternatives, modifications, equivalents and other embodiments, which may be included within the spirit and scope of the disclosure as defined by the appended claims.

A part irrelevant to the description will be omitted to clearly describe the present disclosure, and the same or similar constituent elements will be designated by the same reference numerals throughout the specification. Terms or words used in the specification and the claims should not be interpreted as being limited to a general or dictionary meaning and should be interpreted as a meaning and a concept which conform to the technical spirit of the present disclosure based on a principle that an inventor can appropriately define a concept of a term in order to describe his/her own disclosure by the best method.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

According to an aspect of the present disclosure, there is provided a method of manufacturing a microneedle including steps of spotting a viscous material on a plurality of points on a film by supplying the viscous material on the upper surface of the film through a plurality of through holes (e.g., apertures) disposed on an injection plate, elongating the viscous material spotted on the film, and coagulating the elongated viscous material.

The method may further include a step of surface modifying the film to increase an adhesive force between the viscous material and the film before spotting the viscous material. The surface modifying may be performed by a plasma treatment. During the spotting step, the viscous material may be supplied while the injection plate is closely adhered to the upper surface of the film. The injection plate may be surface treated to lower the adhesive force between the injection plate and the viscous material. The through holes (e.g., apertures) of the injection plate may have widths that is narrower in the lower part than in the upper part.

According to another aspect of the present disclosure, there is provided a method of manufacturing a microneedle including steps of disposing a mask, on which a plurality of through holes are formed, on a film, surface modifying the surface of the film that corresponds to the through holes by plasma treating the film to increase the adhesive force between the film and the viscous material, contacting the surface modified film with the viscous material and separating the film so as for the viscous material to be adhered to the surface modified part of the film, elongating the viscous material adhered to the film, and coagulating the elongated viscous material.

Hereinafter, a method of manufacturing a microneedle and a viscous material supply device for manufacturing a microneedle according to the exemplary embodiments of the present disclosure will be described more fully with reference to the accompanying drawings.

Figure 1:
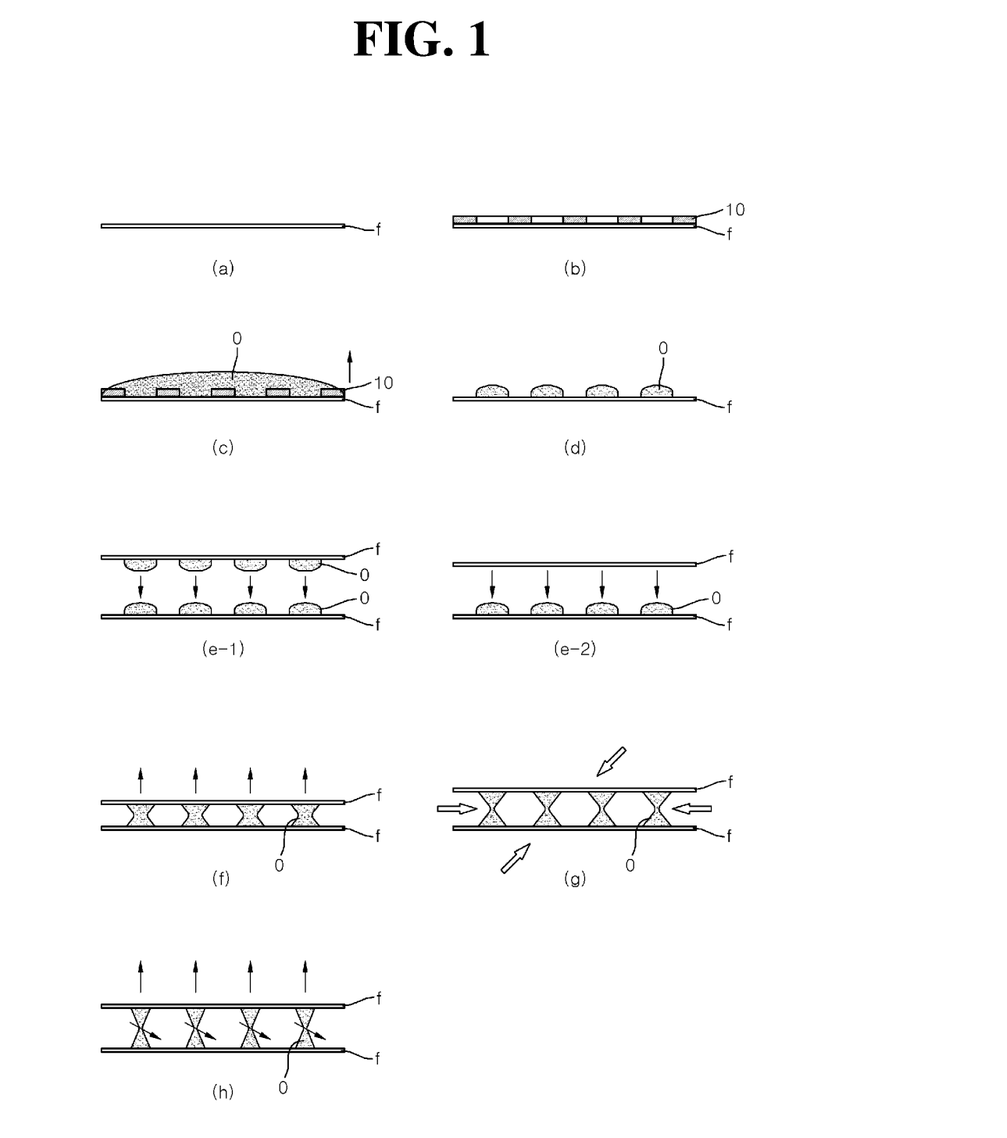
FIG. 1 is a flowchart schematically illustrating a method of manufacturing a microneedle according to an exemplary embodiment of the present disclosure.

FIG. 1 is a flowchart schematically illustrating a method of manufacturing a microneedle according to an exemplary embodiment of the present disclosure.

Firstly, the present disclosure relates to a method of manufacturing a microneedle by using elongating a viscous material. Here, the viscous material may be "a biocompatible or biodegradable material." The "biocompatible material" may denote a non-toxic and chemically inert material. The "biodegradable material" may denote a material which may be biodegraded by body fluid, enzyme, or microorganism in the body.

In addition, the viscous material may be viscous when dissolved by a suitable solvent. That is, although certain viscous material may have viscosity when melted by heat, the viscous material according to the present disclosure may preferably have viscosity when dissolved by a solvent in order to utilize a non-heated process, which is one of the advantages in the present disclosure.

The viscous material described above may include a hyaluronic acid and a salt thereof, polyvinyl pyrrolidone, polyvinyl alcohol, cellulose polymer, dextran, gelatin, glycerin, polyethylene glycol, polysorbate, propylene glycol, povidone, carbomer, gum ghatti, guar gum, glucomannan, glucosamine, dammer resin, rennet casein, locust bean gum, microfibrillated cellulose, psyllium seed gum, xanthan gum, arabino galactan, Arabic gum, alginic acid, gellan gum, carrageenan, karaya gum, curdlan, chitosan, chitin, tara gum, tamarind gum, tragacanth gum, furcelleran, pectin, or pullulan. More preferably, the viscous material used in the present disclosure may be hydroxypropyl methyl cellulose, hydroxyalkyl cellulose, ethyl hydroxyethyl cellulose, alkyl cellulose, carboxymethyl cellulose, and in particular, carboxymethyl cellulose.

In addition, a solvent used to dissolve the viscous material is not particularly restricted and may include water, anhydrous or low-level alcohol with a carbon number of 1-4, acetone, ethyl acetate, chloroform, 1,3-butylene glycol, hexane, diethyl ether, or Butyl Acetate, and more preferably, water or low-level alcohol.

Referring to FIG. 1, the method of manufacturing a microneedle according to an exemplary embodiment of the present disclosure includes spotting, elongating, coagulating, and cutting.

In the spotting, a viscous material may be spotted on a plurality of points on a film. In the present disclosure, the viscous material may be spotted on a plurality of points on a film f once. Here, the film f may be formed of a flexible material so as to be adhered to a skin and may include various forms of film, for example, polyurethane, polyvinyl alcohol, cellulose gum, gelatin, or a film coated by an adhesive composition.

In a basic concept of the spotting, an injection plate 10, on which a plurality of through holes are formed, may be placed on the film f as illustrated in (b) of FIG. 1 while the film f may be firstly placed in (a) of FIG. 1 and then, a viscous material 0 may be supplied to the film f through the through holes of the injection plate 10 ((c) of FIG. 1). Accordingly, the viscous material 0 may be spotted on the plurality of points on the film f ((d) of FIG. 1).

Since the spotting is an important feature in the present disclosure and includes various examples, the spotting will be described in more detail later.

In the elongating, the spotted viscous material 0 may be elongated. Here, as illustrated in (e-1) and (f) of FIG. 1, the two films f, on which the viscous material 0 is spotted respectively, may face each other, the spotted viscous material 0 may contact each other, the two films f may be separated from each other, and then the viscous material 0 may be elongated. In addition, as illustrated in (e-2) and (f) of FIG. 1, the film f (or a plate) may contact with the viscous material 0, the film f may be separated from the other film f, and thereby, the viscous material 0 may be elongated.

In the coagulating, the elongated viscous material 0 may be coagulated. Here, if needed, air may be blown as illustrated in (g) of FIG. 1 and thus, coagulating speed and strength of a microneedle may be increased.

In the cutting, the two films f may be separated from each other rapidly when the viscous material 0 is completely coagulated as illustrated in (h) of FIG. 1. Also, a laser or other cutting tools may be used in the cutting.

According to the present disclosure, modifying of a surface of the film f may be further included before the spotting of the viscous material on the film f. In regard to this, a microneedle may be manufactured by spotting of the viscous material on the film and elongating of the viscous material in the present disclosure. Here, the viscous material may be elongated only when the viscous material is adhered to the surface of the film. Also, the adhesive force between the viscous material and the surface of the film is directly related to the degree of elongation of the viscous material (that is, the shape of a microneedle). Accordingly, it may be desirable that the adhesive force between the viscous material and the surface of the film is uniform and more preferably, over a certain level.

However, types of materials used as a film are practically limited, and a surface of the film is not uniform. Accordingly, in the present disclosure, the film may be plasma processed and thus, the surface may be modified. Therefore, the adhesive force between the viscous material and the film may increase, and the characteristics (e.g., adhesive force) of the surface of the film may become uniform. Then, the viscous material may be elongated uniformly in the elongating process. Types of plasma and intensity may vary according to the type of the film.

According to the present disclosure, the viscous material may be spotted on a plurality of points on the film at the same time and thus, the spotting time may be greatly reduced compared with that in the prior art. Accordingly, the entire process time may be reduced and thus, productivity may be increased.

Also, as the spotting time is reduced, problems occurring due to a difference in viscosity between the viscous materials by evaporation and non-uniformity of a microneedle during elongating may be prevented.

Hereinafter, a device that may be used to spot the viscous material and a process of spotting according to the present disclosure will be described in detail.

Figure 2:
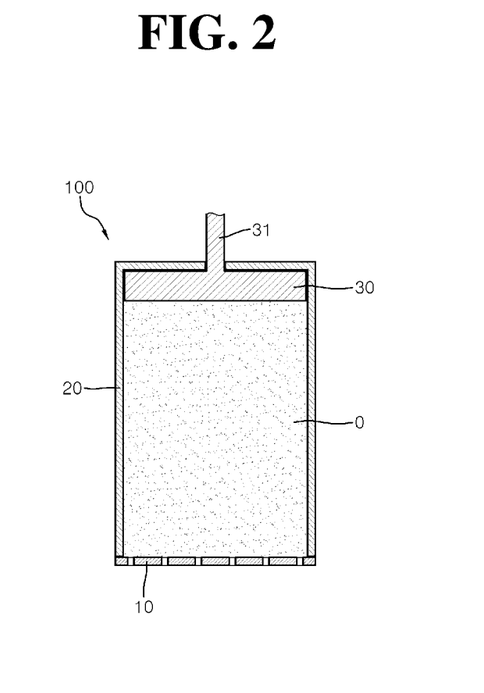
FIG. 2 is a cross-sectional diagram schematically illustrating a viscous material supply device for manufacturing a microneedle according to an exemplary embodiment of the present disclosure.
Figure 3:
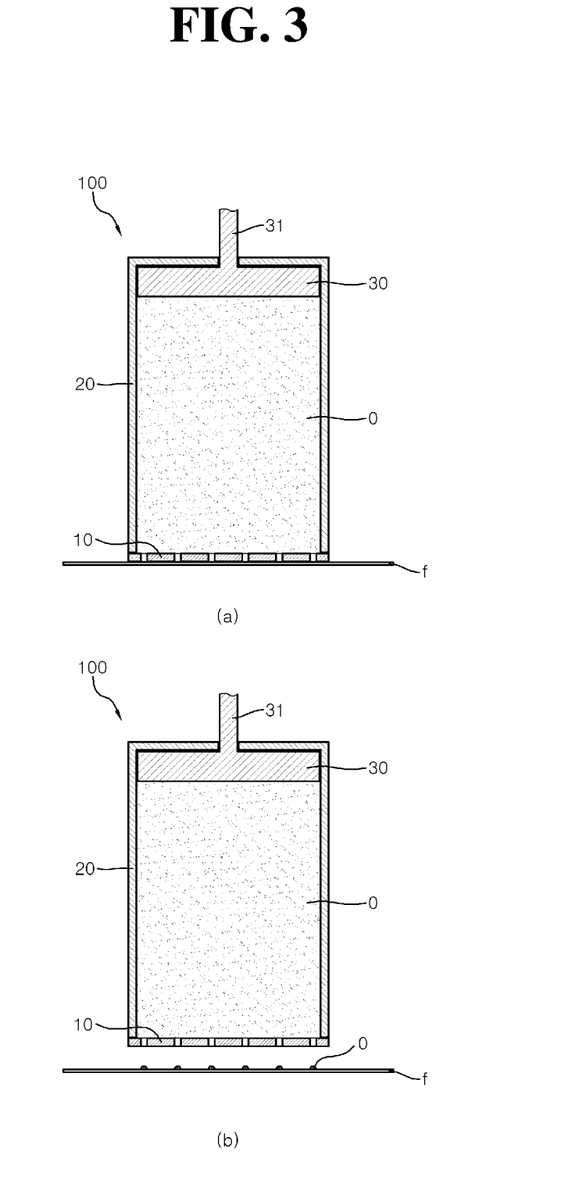
FIGS. 3 and 4 illustrate a process of spotting a viscous material by using the viscous material supply device for manufacturing a microneedle of FIG. 2.
Figure 4:
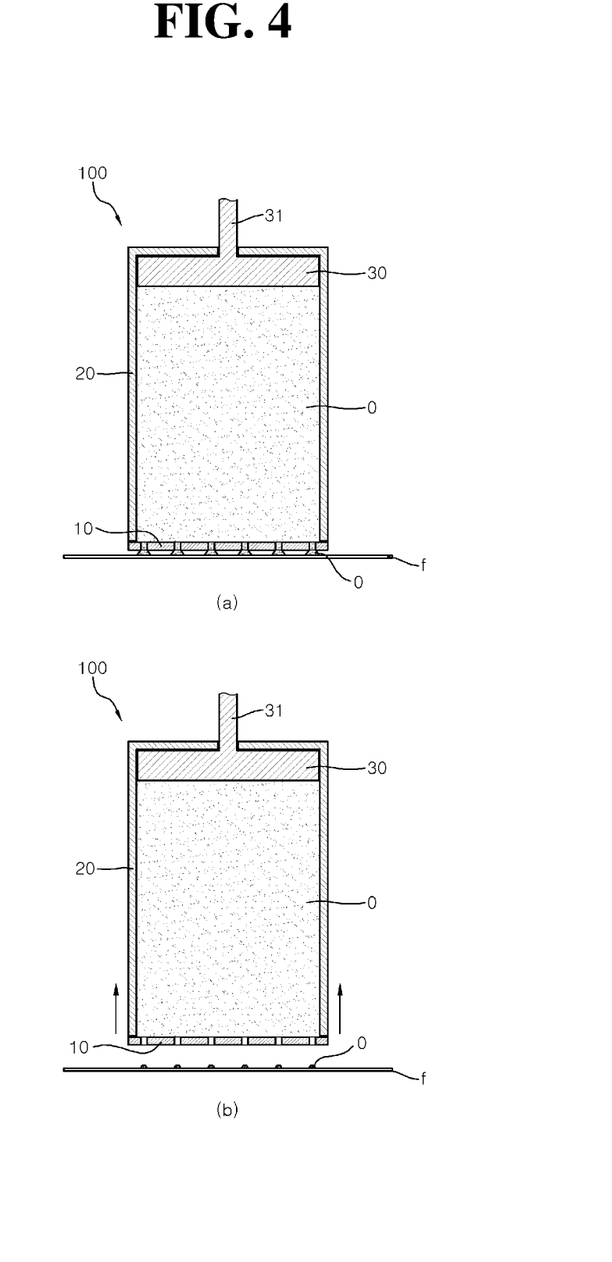

FIG. 2 is a cross-sectional diagram schematically illustrating a viscous material supply device 100 for manufacturing a microneedle according to an exemplary embodiment of the present disclosure, and FIGS. 3 and 4 illustrate a process of spotting the viscous material 0 by using the viscous material supply device 100 of FIG. 2 for manufacturing a microneedle.

Referring to FIG. 2, the viscous material supply device 100 for manufacturing a microneedle is configured to supply the viscous material 0 on a plurality of points, which may be spaced apart from each other, on the film f. The viscous material supply device 100 for manufacturing a microneedle according to the current exemplary embodiment of the present disclosure may include a main body part 20, an injection plate 10, and a pressure means.

In the main body part 20, a space for storing the viscous material 0 may exist and one end of the main body part 20 may be opened. The injection plate 10 may be formed of a plate and may include a plurality of through holes penetrating therethrough. The injection plate 10 is configured to be combined to the one end (the opened part) of the main body part 20. The pressure means is configured to apply pressure so that the viscous material 0 stored in the main body part 20 may be discharged through the through holes. In the current embodiment of the present disclosure, the pressure means may be a piston structure. In particular, a pressurizing plate 30 may be disposed in the main body part 20. When the pressurizing plate 30 moves to the lower part by a drive shaft 31, the viscous material 0 may be discharged through the through holes. Also, it is important that a uniform amount of the viscous material 0 is discharged. Accordingly, a form of the pressure means may be changed into various means as mentioned above.

The injection plate 10 may be surface treated so that the adhesive force between the viscous material 0 and the injection plate 10 may be minimized. When the viscous material 0 is strongly adhered to the through holes of the injection plate 10, the viscous material 0 is coagulated while the viscous material 0 is adhered to the through holes, and thus the through holes are blocked. In this case, there may be a deviation in the amount of discharged viscous material 0. Therefore, the injection plate 20 (in particular, including parts of the through holes) according to the current exemplary embodiment of the present disclosure may be coated with a hydrophobic material, for example, PU or Teflon. As a reference, a hydrophobic material may be used because a large number of viscous materials are aqueous solution. According to a feature of the viscous material, a surface treatment may be appropriately changed.

In the spotting of the viscous material 0 by using the viscous material supply device 100 for manufacturing a microneedle, the injection plate 10 may be completely adhered to the upper surface of the film f, as illustrated in (a) of FIG. 3. Here, the viscous material supply device 100 for manufacturing a microneedle may be pressurized to the lower part so that the injection plate 10 may be adhered to the film f, or an electromagnetic force (between a stage, on which the film f is placed (not illustrated) and the injection plate 10) may be used to adhere the injection plate 10 to the film f. Here, when the viscous material 0 is pressurized, the viscous material 0 may fully fill the through holes, and a part of the viscous material 0 may be adhered to the upper surface of the film f. Then, when the pressure is stopped and the viscous material supply device 100 for manufacturing a microneedle is lifted up, the viscous material 0 may be spotted on a plurality of points on the film f, as illustrated in (b) of FIG. 3. As described above, because the adhesive force between the film f and the viscous material 0 is treated in a way to be made strong, and an adhesive force between the injection plate 10 and the viscous material 0 is treated to be weak, more than a certain amount of the viscous material 0 may be adhered to the surface of the film f and remains on the film f. In order to adjust the amount of remaining viscous material 0, the size or shape of the through holes may be appropriately changed.

As illustrated in FIG. 4, while the viscous material supply device 100 for manufacturing a microneedle is separated from the film f, a certain amount of viscous material 0 may be discharged and then, the viscous material supply device 100 for manufacturing a microneedle may be lifted up. However, in this case, a precise pressure means is needed so that the amount of viscous material 0 discharged through the through holes may be uniform.

Figure 5:
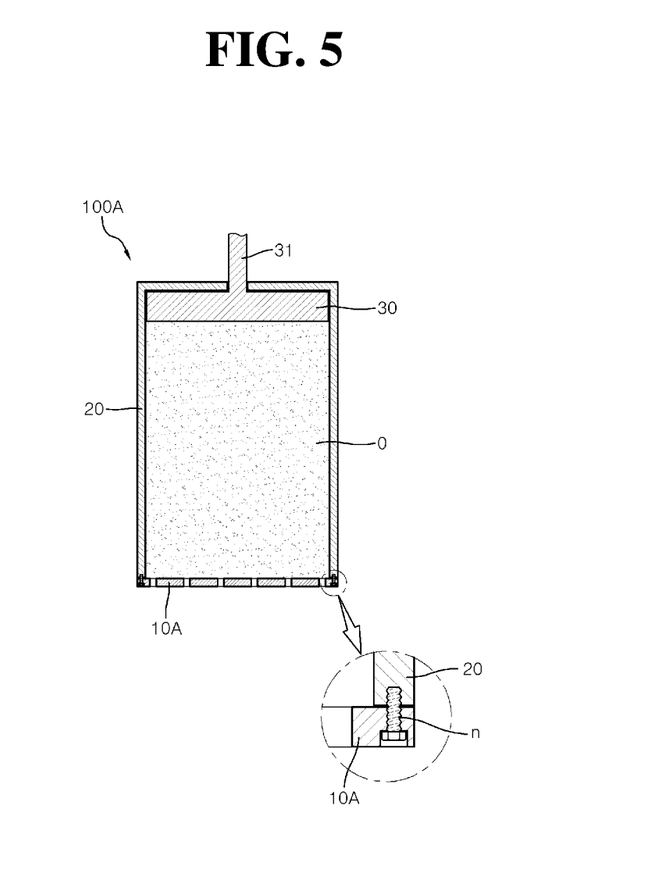
FIGS. 5 and 6 are cross-sectional diagrams schematically illustrating viscous material supply devices for manufacturing a microneedle according to other exemplary embodiments of the present disclosure.
Figure 6:
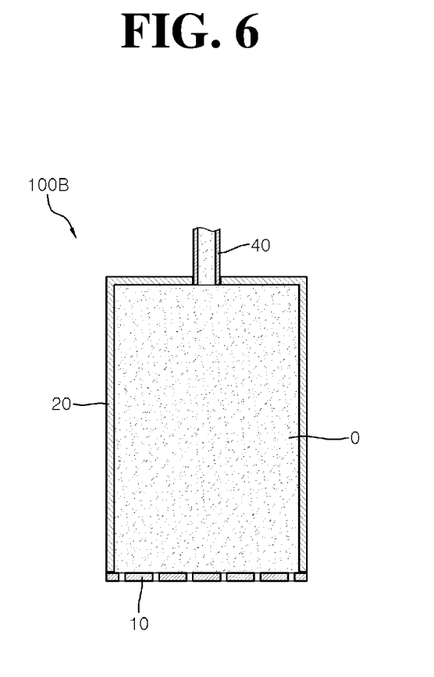

FIGS. 5 and 6 are cross-sectional diagrams schematically illustrating viscous material supply devices 100A and 100B for manufacturing a microneedle according to other exemplary embodiments of the present disclosure.

Referring to FIG. 5, an injection plate 10A may be detachably coupled to the main body part 20 by a screw n. In particular, as illustrated in an enlarged part of FIG. 5, the injection plate 10A may include a groove (e.g., recess or counterbore), into which the screw n may be inserted, and the head of the screw n may be completely inserted (e.g., flush) into the groove. Accordingly, the injection plate 10A may be completely adhered to a film.

Referring to FIG. 6, a supply pipe 40 for supplying the viscous material 0 may be connected to the main body part 20. Through this supply pipe 40, a certain amount (or certain pressure) of viscous material 0 may be supplied and then, the viscous material 0 may be discharged through the through holes. As a reference, a certain amount of the viscous material 0 may be continuously supplied, however, more preferably, the viscous material 0 may be supplied in a pulse mode, wherein the viscous material 0 may be supplied at a specific time.

In addition, the viscous material 0 may be supplied on the film by using the viscous material supply devices 100A and 100B for manufacturing a microneedle of FIGS. 5 and 6 as in the same manner as the viscous material supply device 100 for manufacturing a microneedle of FIGS. 3 and 4.

Figure 7:
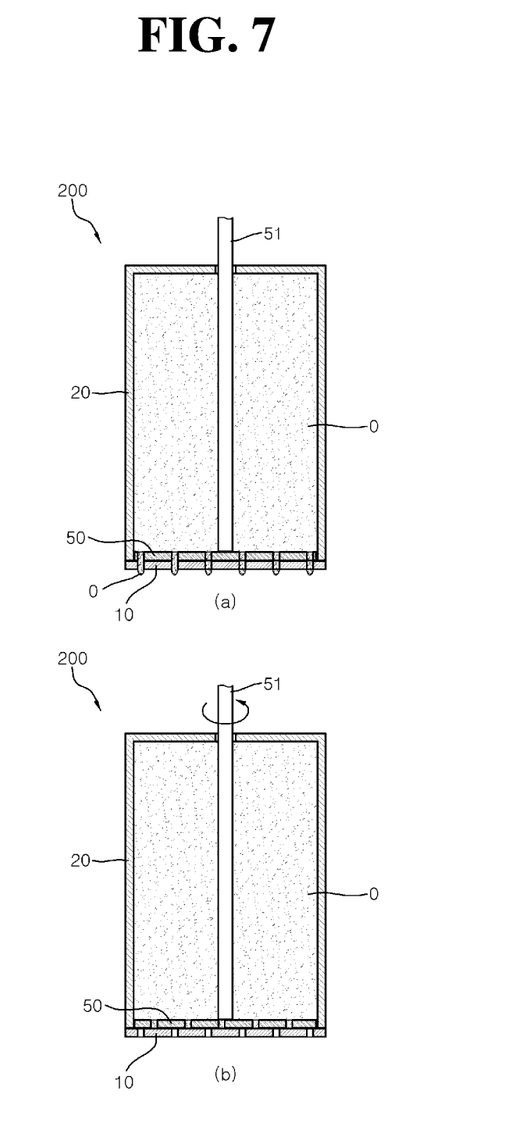
FIG. 7 is a cross-sectional diagram schematically illustrating a viscous material supply device for manufacturing a microneedle according to another exemplary embodiment of the present disclosure.
Figure 8:
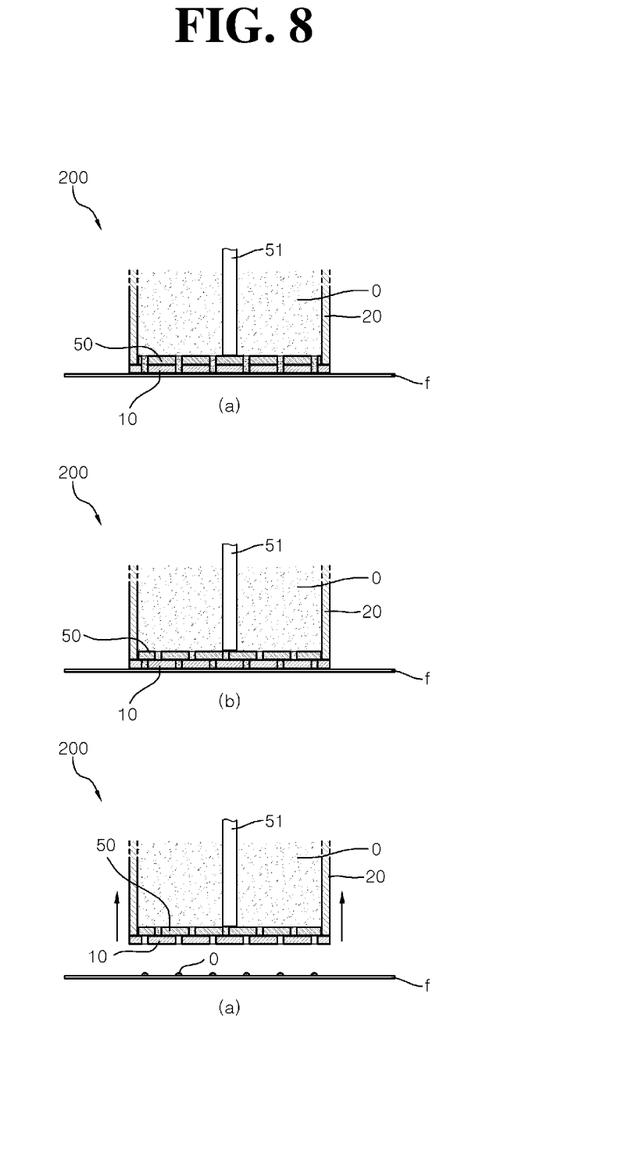
FIG. 8 illustrates a process of spotting a viscous material by using the viscous material supply device for manufacturing a microneedle of FIG. 7.

FIG. 7 is a cross-sectional diagram schematically illustrating a viscous material supply device 200 for manufacturing a microneedle according to another exemplary embodiment of the present disclosure, and FIG. 8 illustrates a process of spotting the viscous material 0 by using the viscous material supply device 200 for manufacturing a microneedle of FIG. 7.

Referring to FIG. 7, the viscous material supply device 200 for manufacturing a microneedle may include the main body part 20, the injection plate 10, the pressure means, and an opening and closing part 50.

In the main body part 20, a space for storing the viscous material 0 may exist, and one end of the main body part 20 may be opened. The injection plate 10 may be formed of a plate and include a plurality of through holes penetrating therethrough. The injection plate 10 may be combined to the one end (the opened part) of the main body part 20. The pressure means is configured to apply pressure so that the viscous material 0 stored in the main body part 20 may be discharged through the through holes. In the current exemplary embodiment, although not illustrated in the drawing, the pressure means may be a supply pipe as in FIG. 6 for supplying the viscous material 0 in the main body part 20.

In addition, the opening and closing part 50 may be used to open and close the through holes. In the current exemplary embodiment of the present disclosure, the opening and closing part 50 may be formed of a circular plate and disposed on the upper side of the injection plate 10 within the main body part 20. The opening and closing part 50 may include a plurality of opening and closing holes (e.g., apertures) penetrating therethrough, each of which may correspond to the through holes of the injection plate 10. The opening and closing part 50 may be connected to a rotation axis 51 and configured to move between an open position and a closed position as the rotation axis 51 rotates. As illustrated in (a) of FIG. 7, the opening and closing holes and the through holes are configured to respectively face each other and accordingly, the open position is where the viscous material 0 in the main body part 20 may be discharged through the through holes. Also, the closed position is where the through holes are blocked by the opening and closing part 50 since the opening and closing holes and the through holes are disposed alternately as illustrated in (b) of FIG. 7. Here, in the closed position, the viscous material 0 may not be supplied through the through holes.

In the current exemplary embodiment of the present disclosure, the through holes may be opened or closed based on the rotation of the opening and closing part 50. However, the through holes may be opened or closed based on a sliding of the opening and closing part 50.

Supplying of the viscous material 0 by using the viscous material supply device 200 for manufacturing a microneedle according to the current exemplary embodiment of the present disclosure will be described. Referring to FIG. 8, the injection plate 10 may be completely adhered to the film f, and the viscous material 0 may be supplied through the pressure means while the opening and closing part 50 is disposed in the open position. Then, as illustrated in (a) of FIG. 8, the viscous material 0 may fully fill the through holes of the injection plate 10 and thus, a part of the viscous material 0 may contact the film f. In this state, as illustrated in (b) of FIG. 8, when the opening and closing part 50 rotates toward the closed position, the viscous material 0 may not be supplied through the through holes of the injection plate 10.

Then, as illustrated in (c) of FIG. 8, when the injection plate 10 is lifted up, the viscous material 0 existing in the through holes of the injection plate 10 may remain and be adhered to the film f and thus, the viscous material 0 may be spotted on a plurality of points. For example, when the adhesive force between the film f and the viscous material 0 is treated to be strong, and the adhesive force between the injection plate 10 and the viscous material 0 is treated to be weak, most of the viscous material 0 may be spotted and remain on the film f.

According to the current exemplary embodiment of the present disclosure, the amount of the viscous material spotted at a time may be determined based on the volume of the through holes of the injection plate (more preferably, the amount of the supplied viscous material is the same as the volume of the through holes) and accordingly, the viscous material with a constant amount may be spotted. In particular, when the viscous material is injected through the plurality of through holes at the same time as in the current exemplary embodiment of the present disclosure, it is important that the amount of the viscous material injected from each through hole is uniform. Controlling an injection amount by an injection pressure control (that is, performance of the pressure means) requires an advanced skill and also is challenging. However, according to the current exemplary embodiment of the present disclosure, the amount of the injected viscous material may be constant and accurate based on the shape (volume) of the through holes.

Figure 9:
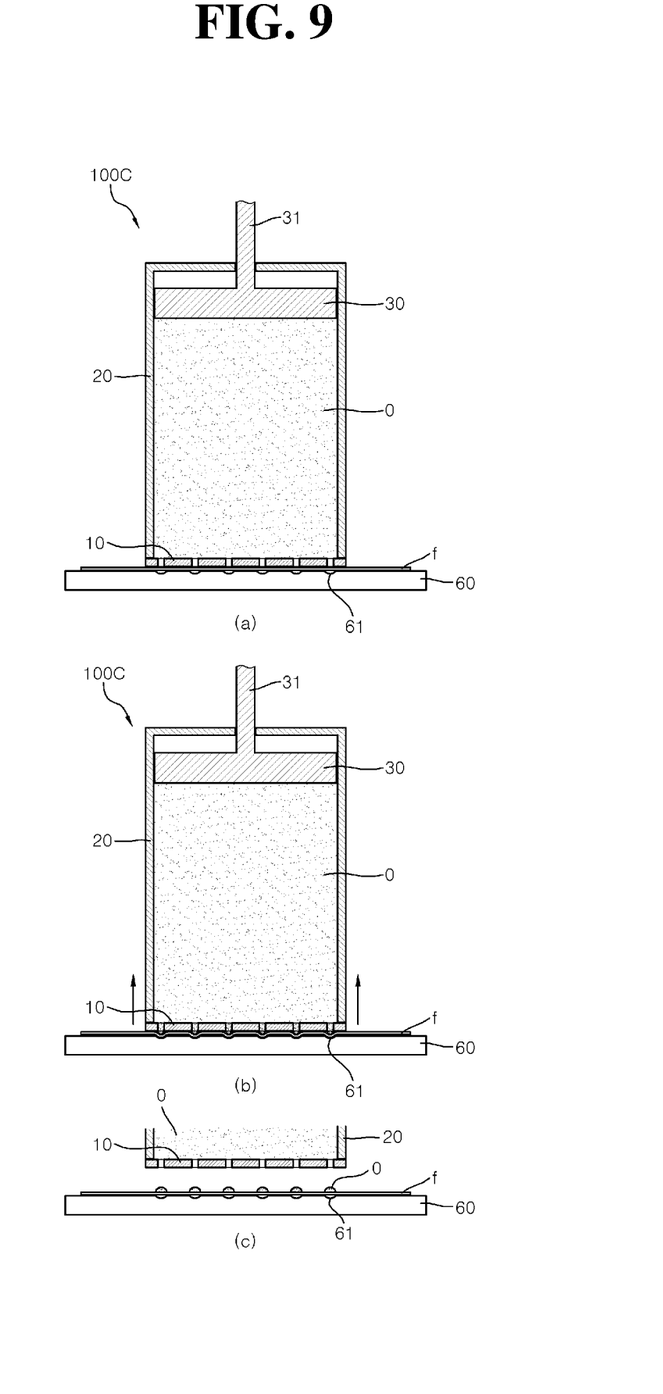
FIG. 9 illustrates a process of supplying a viscous material by using a viscous material supply device for manufacturing a microneedle according to another exemplary embodiment of the present disclosure.

FIG. 9 illustrates a process of supplying the viscous material 0 by using a viscous material supply device 100C for manufacturing a microneedle according to another exemplary embodiment of the present disclosure.

Referring to FIG. 9, the viscous material supply device 100C for manufacturing a microneedle according to the current exemplary embodiment of the present disclosure may further include a stage 60.

The stage 60 is where the film f may be disposed and may include a plurality of filling grooves 61 on the upper surfaces thereof. The filling grooves 61 may be concave toward the lower part and be formed to respectively correspond to the through holes of the injection plate 10.

In the supplying of the viscous material 0, the injection plate 10 may be completely adhered to the film f while the film f is disposed on the stage 60 as illustrated in (a) of FIG. 9. In this state, when the viscous material 0 is supplied, the film f may be pushed and enter the filling grooves 61 due to pressure of supplying the viscous material 0, and the viscous material 0 may fill the filling grooves 61 as illustrated in (b) of FIG. 9. Then, when the supplying of the viscous material 0 is stopped and the injection plate 10 is lifted up, the viscous material 0 may be spotted as illustrated in (c) of FIG. 9. For reference, as the film f has elasticity at a certain level, the film f may be restored after entering the filling grooves 61.

In comparison between the current exemplary embodiment and the embodiment of FIG. 3, the viscous material 0 may be spotted as much as the volume of the through holes in FIG. 3, whereas more viscous material 0 may be spotted due to the volume of the filling groove 61. Accordingly, the amount of spotted viscous material may be changed by the shape of the filling grooves.

In the process of injecting the viscous material 0 described above, when the lower surface of the injection plate 10 (more specifically, the edge of the through holes) is stained by the viscous material 0 (for example, the viscous material 0 may leak outside through the through holes and stained the lower edge of the through holes), the viscous material 0 is hardened, and this can damage the following processes. Accordingly, in the present disclosure, such a problem may be solved by a change in the shape of the through holes.

Figure 10:
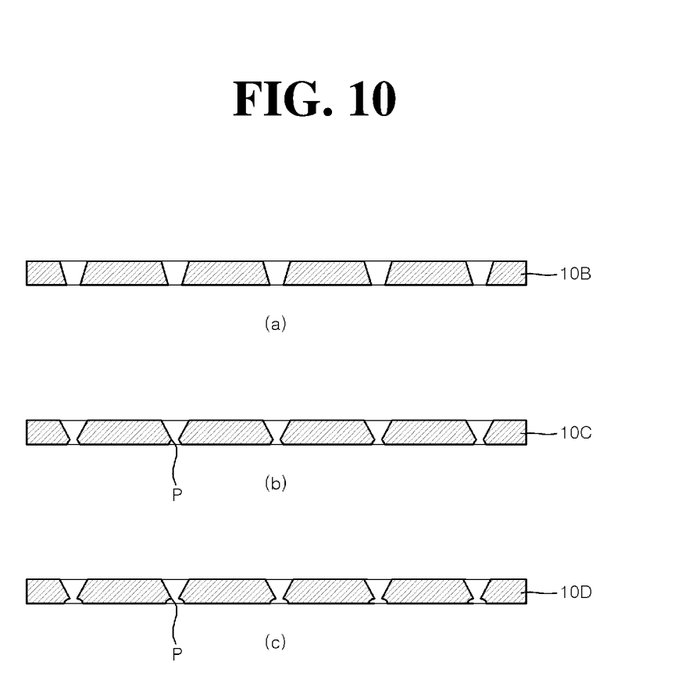
FIG. 10 is a cross-sectional diagram of an injection plate according to another exemplary embodiment of the present disclosure.

FIG. 10 is a cross-sectional diagram of an injection plate 10B according to another exemplary embodiment of the present disclosure.

Referring to (a) of FIG. 10, through holes of the injection plate 10B may be formed in a shape similar to an inverted triangle, in which the width (e.g., diameter) thereof becomes gradually narrow as it goes from the upper surface to the lower surface. When the viscous material is pushed to the through holes by applying pressure to the viscous material, and the applying pressure is released, the viscous material existing in the through holes may be sucked up (e.g., drawn back in or retreated) due to viscosity. Here, since the width of the lower part of the through holes is narrower than that of the upper part, the viscous material may be retreated by a longer distance in the lower part of the through holes, even if the viscous material is retreated by a small distance in the upper part. Accordingly, the viscous material may be prevented from leaking outside and staining the lower surface of the injection plate.

Referring to (b) and (c) of FIG. 10, widths of through holes in injection plates 10C and 10D may become gradually narrower from the upper surface toward the lower surface and widen again below a specific position p. When the through holes are formed as described above, the viscous material is supplied to a film through the through holes, and then, the injection plates 10C and 10D are lifted up while the supplying of the viscous material is stopped, the viscous material remaining in the through holes may be separated at the specific point P. Then, the viscous material existing below the specific position P may be adhered to the film f, and the viscous material existing above the specific position P may remain in the through holes. In addition, when the viscous material leaks through the through holes, the viscous material flows along the inner walls of the through holes. In the current exemplary embodiment, widths of the inner walls of the through holes widen after the specific point P and thus, the viscous material may be prevented from flowing.

Figure 11:
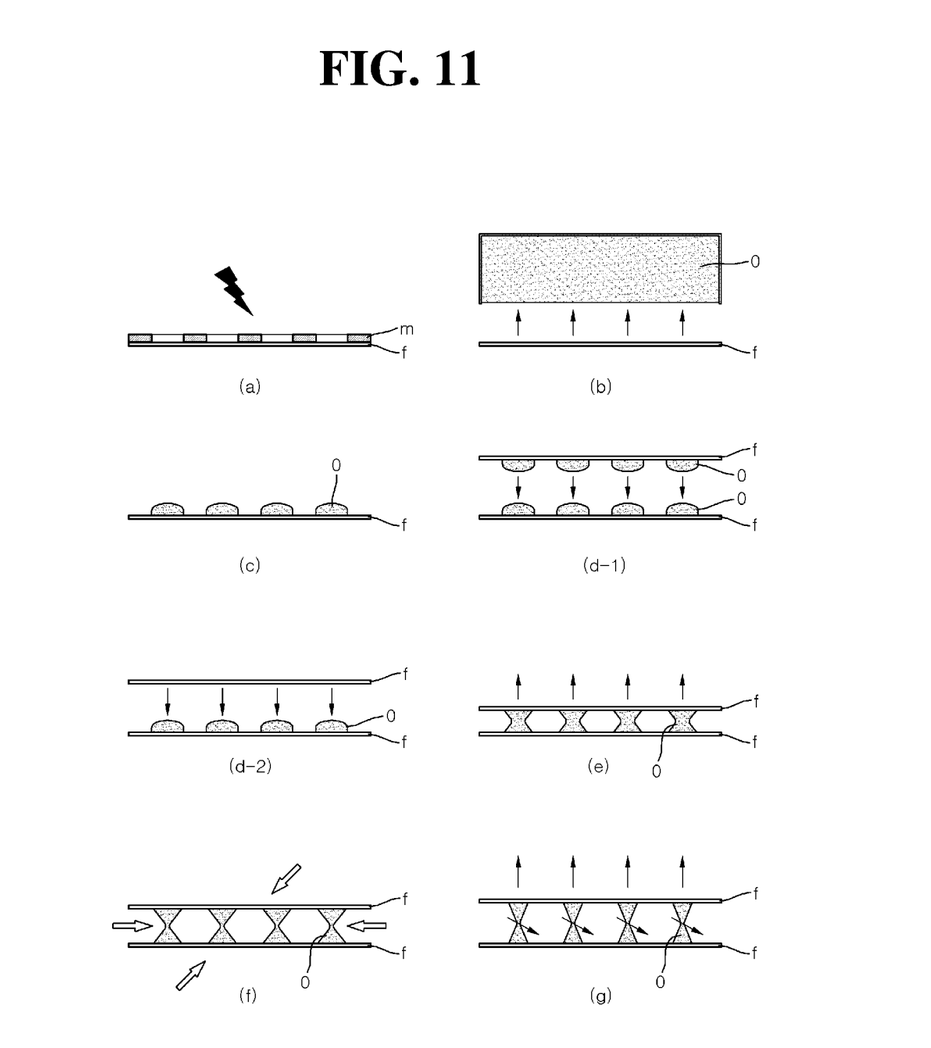
FIG. 11 is a flowchart of a method of manufacturing a microneedle according to another exemplary embodiment of the present disclosure.

FIG. 11 is a flowchart of a method of manufacturing a microneedle according to another exemplary embodiment of the present disclosure.

Referring to FIG. 11, the method of manufacturing a microneedle according to the current exemplary embodiment of the present disclosure may include spotting, elongating, coagulating, and cutting. The processes except for the spotting are the same as those described with reference to FIG. 1 above. Therefore, only the spotting will be described in detail below.

According to the current exemplary embodiment of the present disclosure, as illustrated in (a) of FIG. 11, a mask m, on which a plurality of through holes are formed, may be disposed on the film f, and a plasma treatment may be performed. Then, only the part that is exposed to the plasma, that is, the surface of the film corresponding to the through holes may be modified. Accordingly, the adhesive force between this part (that is, the part that has been surface modified) and the viscous material may increase.

Then, as illustrated in (b) of FIG. 11, when the film f contacts with the viscous material 0 and then is separated, the viscous material 0 may be only adhered to the part having high adhesive force with the viscous material, that is, the part that has been surface modified and accordingly, the viscous material 0 may be spotted as illustrated in (c) of FIG. 11.

Then, as described above with reference to FIG. 1, elongating, coagulating, and cutting may be performed to manufacture a microneedle.

According to the present disclosure, the viscous material may be easily and simply spotted on the film (without the viscous material supply devices for manufacturing a microneedle described above).

However, when the film contacts the viscous material, the viscous material may partly stain the part that is not surface modified). To overcome this problem, a material having a low adhesive force with the viscous material may be used to manufacture a film, or the rest of the surface that is not surface modified may be treated to have a lower adhesive force with the viscous material.

According to the present invention, the time for spotting the viscous material may be reduced and thus, deterioration due to a viscosity deviation may be prevented. Also, production efficiency may increase.

While the present disclosure has been particularly shown and described with reference to exemplary embodiments thereof, it will be understood by those of ordinary skill in the art that various changes in form and details may be made therein without departing from the spirit and scope of the present disclosure as defined by the following claims.

The invention claimed is:

1. A method of manufacturing a microneedle comprising:
   disposing a film on a stage, wherein the stage includes a plurality of filling grooves formed concavely on an upper surface thereof;
   adhering an injection plate to an upper surface of the film to align through holes of the injection plate to respectively correspond to the plurality of filling grooves;
   spotting a viscous material on a plurality of points on the film by supplying the viscous material on the upper surface of the film through the through holes;
   elongating the viscous material spotted on the film; and
   coagulating the elongated viscous material,
   wherein the injection plate is surface treated to lower an adhesive force between the injection plate and the viscous material.

* * * * *